United States Patent
Ferrari et al.

(10) Patent No.: US 9,757,328 B2
(45) Date of Patent: Sep. 12, 2017

(54) LYSOZYME GEL FORMULATIONS

(71) Applicants: Stefano Ferrari, Rhinebeck, NY (US); Roelof Rongen, Califon, NJ (US)

(72) Inventors: Stefano Ferrari, Rhinebeck, NY (US); Roelof Rongen, Califon, NJ (US)

(73) Assignee: Murami Pharma, Inc., Rhinebeck, NY (US)

( * ) Notice: Subject to any disclaimer, the term of this patent is extended or adjusted under 35 U.S.C. 154(b) by 0 days.

(21) Appl. No.: 13/833,773

(22) Filed: Mar. 15, 2013

(65) Prior Publication Data

US 2013/0259852 A1 Oct. 3, 2013

Related U.S. Application Data

(60) Provisional application No. 61/617,194, filed on Mar. 29, 2012, provisional application No. 61/749,318, filed on Jan. 6, 2013.

(51) Int. Cl.
| | |
|---|---|
| *A61K 9/06* | (2006.01) |
| *A61K 9/00* | (2006.01) |
| *A61K 38/47* | (2006.01) |
| *A61K 45/06* | (2006.01) |
| *A61K 47/10* | (2017.01) |

(52) U.S. Cl.
CPC .............. *A61K 9/0014* (2013.01); *A61K 9/06* (2013.01); *A61K 38/47* (2013.01); *A61K 45/06* (2013.01); *A61K 47/10* (2013.01)

(58) Field of Classification Search
USPC .............................. 424/94.61, 267
See application file for complete search history.

(56) References Cited

U.S. PATENT DOCUMENTS

| | | | | |
|---|---|---|---|---|
| 6,056,955 | A | * | 5/2000 | Fischetti et al. .............. 424/94.1 |
| 2005/0203333 | A1 | * | 9/2005 | Dailey et al. .................. 600/37 |
| 2009/0238811 | A1 | * | 9/2009 | McDaniel et al. ........... 424/94.2 |
| 2010/0329995 | A1 | * | 12/2010 | Deeter et al. .................. 424/45 |
| 2011/0200678 | A1 | * | 8/2011 | Hwang et al. ................ 424/489 |
| 2012/0164087 | A1 | * | 6/2012 | Carter ............................. 424/60 |

OTHER PUBLICATIONS

Pastor I. et al. Structure and Dynamics of Lysozyme Encapsulated in a Silica Sol-Gel Matrix. J Physical Chemistry 111(39)11603-11610, Oct. 4, 2007.*
Egg (food), Wikipedia online, Apr. 9, 2014.
Houen G, Acta Chemica Scandinavica, 1996 (50):68-70.

* cited by examiner

*Primary Examiner* — Ralph Gitomer
(74) *Attorney, Agent, or Firm* — Norris McLaughlin & Marcus, P.A.

(57) ABSTRACT

The present invention relates to formulations of gelled lysozyme achieved by the addition of water to a lysozyme suspension in a solvent, such as an alcohol, with retention of enzymatic activity. It was surprisingly discovered that lysozyme itself is a gelling substance (self-gel) and, therefore, it can be advantageously formulated into topical compositions without the addition of other gelling substances such as cellulose, starch or other polysaccharides. The activity of the lysozyme is enhanced as compared to other formulations of comprising lysozyme. The formulations contained in the present invention are useful in methods in the fields of therapeutics, disinfectants, sanitizers, personal hygiene, and cosmetics for human and veterinary use.

12 Claims, No Drawings

LYSOZYME GEL FORMULATIONS

CROSS-REFERENCE TO RELATED APPLICATIONS

This application claims priority of U.S. Provisional Application No. 61/749,318, filed Jan. 6, 2013, and U.S. Provisional Application No. 61/617,194, filed Mar. 29, 2012, the entire contents of which applications are fully incorporated herein by reference.

BACKGROUND OF THE INVENTION

1. Field of the Invention

The present invention relates to formulations of gelled lysozyme, achieved by the addition of water to a lysozyme suspension in a solvent, such as an alcohol. In fact, it was surprisingly discovered that lysozyme itself is a gelling substance (self-gel) and, therefore, it can be advantageously formulated into topical compositions without the addition of other gelling substances such as cellulose, starch or other polysaccharides. The activity of the lysozyme is enhanced as compared to other formulations comprising lysozyme. The formulations contained in the present invention are useful in the fields of therapeutics, disinfectants, sanitizers, personal hygiene, and cosmetics for human and veterinary use.

2. Description of Related Art

"Lysozyme", also known as muramidase, is part of the innate immune system and is intended as a family of enzymes that catalyze the hydrolysis of mucopolysaccharides that form the cellular wall of bacteria, causing their lysing. The term "lysozyme" includes lysozymes of natural origin, like the one present in hen-egg-white and many other animal species, but also synthetic lysozymes and recombinant lysozymes, like human recombinant lysozyme. Lysozyme is widely present in the animal and plant kingdoms, in particular in algae, bacteria, fungi and certain metazoa. In humans it is present in various physiological fluids, tissues and organs such as milk, saliva, placenta, spleen, leukocytes, tears, serum, etc, where it performs fundamental functions such as part of the immune function in the protection from infections. Industrially, lysozyme is often obtained by extraction from hen-egg-whites as free base or as an organic or inorganic salt, preferably as a hydrochloride. Lysozyme, free-base or in a hydrochloride form, is soluble in water. The resulting solution does not show particular rheological properties as, for example, significant viscosity values. Lysozyme base or hydrochloride is practically insoluble in common organic solvents, like ethanol, methanol, dioxane, mercaptoethanol or isoamyl alcohol (see below).

TABLE 1

Solubility of lysozyme in various organic solvents.

| Solvent | Solubility/ mg ml$^{-1}$ | Solubility/ µM | Comments |
|---|---|---|---|
| Acetic acid | 0.55 | 38.46 | clear supernatant |
| Acetonitrile | 0.03 | 2.10 | clear supernatant |
| Benzene | 0.02 | 1.40 | clear supernatant |
| Butanol | 0.03 | 2.10 | clear supernatant |
| Butyl chloride | 0.08 | 5.59 | clear supernatant |
| Chloroform (1% EtOH) | 0.25 | 17.48 | clear sup., some dissolved |
| N-Dimethylformamide | 0.61 | 42.66 | clear supernatant |
| Dimethyl sulfoxide | >100 | >7000 | clear sup., all dissolved |
| Dioxane | 0.02 | 1.40 | clear supernatant |

TABLE 1-continued

Solubility of lysozyme in various organic solvents.

| Solvent | Solubility/ mg ml$^{-1}$ | Solubility/ µM | Comments |
|---|---|---|---|
| Ethanol | 0.02 | 1.40 | clear supernatant |
| Formic Acid | >100 | >7000 | all dissolved |
| Glycerol | >100 | >7000 | all dissolved |
| Heptane | 0.02 | 1.40 | clear supernatant |
| Isoamyl alcohol | 0.08 | 5.59 | clear supernatant |
| 2-Propanol | 0.07 | 4.90 | clear supernatant |
| 2-Mercaptoethanol | 0.65 | 45.45 | clear sup., some dissolved |
| 3-Mercaptopropionic acid | 4.20 | 293.71 | clear sup., much dissolved |
| Methanol | 0.01 | 0.70 | clear supernatant |
| 1-Propanol | 0.02 | 1.40 | clear supernatant |
| Triethanolamine | 0.88 | 55.94 | clear supernatant |
| Trifluoroacetic acid | >100 | >7000 | all dissolved |

Source: Houen G, Acta Chemica Scandinavica, 1996 (50): 68-70

SUMMARY OF THE INVENTION

It has been surprisingly found, embodied in the present invention, that lysozyme, as a free base or as a salt, preferably a hydrochloride, acts as a gelling (self-gelling) substance in mixtures of a solvent in which lysozyme is not soluble and which solvent is readily mixable with water (including alcohols such as ethanol) and water. To further surprise, lysozyme in this self-gel form has a higher activity than other forms of lysozyme (see Example 6). Those commonly skilled in the art would typically expect an inactivating or denaturing effect of an alcohol on a protein, not an enhancement of activity.

Accordingly, the present invention relates in a first embodiment to a composition comprising gelled lysozyme, water and a solvent, wherein the gelled lysozyme retains activity or has an enhanced activity. Lysozyme has a broad range of activities including, but not limited to, enzymatic activity (e.g. muramidase activity), immune-modulating activity, and activity in interacting with the central nervous system. In some embodiments, the gelled lysozyme retains activity compared to the lysozyme precursor that was not gelled in a manner comprised by the current invention or any essentially equivalent manner by least 25% of at least one activity of the lysozyme precursor, preferably at least 50% of at least one activity of the lysozyme precursor, more preferably at least 75% of at least one activity of the lysozyme precursor, more preferably at least 90% of at least one activity of the lysozyme precursor, preferably at least 95% of at least one activity of the lysozyme precursor, most preferably at least 100% of at least one activity of the lysozyme precursor. In other embodiments, the activity of the gelled lysozyme is enhanced as compared to the activity of lysozyme not gelled in a manner comprised by the current invention or any essentially equivalent manner by at least 5%, more preferably at least 10%, more preferably at least 12%, more preferably at least 14%, more preferably at least 16%, more preferably at least 18%, more preferably at least 20%, more preferably at least 22%, more preferably at least 25%, more preferably at least 30%, more preferably at least 40%, most preferably at least 50%.

The present invention relates in a second embodiment to a process of preparing the composition of the invention, comprising suspending lysozyme in a solvent to form a suspension and adding water to the suspension to form a gel.

The present invention relates in a third embodiment to a method of treating a disease or disorder treatable with lysozyme, comprising administering an effective amount therefor of the composition of the invention to a patient in need of such treating.

DETAILED DESCRIPTION OF THE INVENTION

The choice of the solvent in the gel may depend on its intended use, including the rheological characteristics that one wants to give the gel, the required low toxicity level of such gel, and potential features embodied in the choice of the solvent. In some embodiments of the present invention, the solvent has low toxicity characteristics and is chosen from ethanol, methanol, propanol, butanol, isopropyl alcohol, isobutyl alcohol, isoamyl alcohol, isopropylalcohol, benzylalcohol, or polyvinylalcohol and other solvents with similar relatively low toxicity. In other embodiments, the solvent has higher toxicity characteristics and is chosen from dioxane, mercaptoethanol, acetonitrile, and other solvents with more significant toxic or carcinogenic properties. With the disclosure of the present invention, a person with ordinary skill in the art will be able to test and select such solvents which have relatively low toxicological properties and are suitable for topical application to humans or animals.

The concentration of lysozyme in the gel can be within a range of values, which depends on the rheological characteristics that one wants to give the gel and the intended use of such gel. In some embodiments of the present invention, the amount of lysozyme comprises between 0.1% w/w and 50% w/w of the total gel, more preferably between 0.2% w/w and 40% w/w, more preferably between 0.3% w/w and 30% w/w, more preferably between 0.5% w/w and 20% w/w, more preferably between 1% w/w and 10% w/w, more preferably between 1.5% w/w and 8% w/w, more preferably between 2% w/w and 6% w/w, more preferably between 1% w/w and 5% w/w, more preferably between 3% w/w/ and 6% w/w, preferably between 2% w/w and 5% w/w, most preferably between 3% w/w and 5% w/w.

Also the water concentration in the mix with the solvent can be within a range of values, and depends on the rheological characteristic that one wants to give the gel and the intended use of such gel. In some embodiments of the present invention, the amount of water comprises between 1% w/w and 95% w/w of the total gel, more preferably between 2% w/w and 80% w/w, more preferably between 5% w/w and 60% w/w, more preferably between 10% w/w and 50% w/w, most preferably between 20% w/w and 40% w/w.

The lysozyme gels, as embodied in the present invention, have advantageous properties, particularly useful for the intended uses as topical applications for human and veterinary use. In particular, it should be emphasized that the invented formulations do not require the presence of preservatives, gelling agents, thickeners, sequestering agents, etc. Consequently, the use of such topical applications is safer and more economical. In addition, the gels from the present invention leave minimal residue upon application and drying.

The lysozyme gels, as embodied in the present invention, are particularly useful for therapeutic use, like for example in the topical treatment of sores, bed sores, diabetic skin ulcerations, ulcerations from peripheral vascular disease, wounds, abscesses, pimples, acne, burns, insect bites, thorn punctures, contact from jellyfish, podiatric interventions (diabetic foot, ingrown toenail, calluses, etc.), gingivitis, stomatitis, breast fissures, hand and foot fissures, in otology, etc.

In particular, the lysozyme gels, as embodied in the present invention, have surprisingly shown to have a markedly increased activity of the lysozyme as evidenced, for instance, by the stimulating activity in the synthesis of mucopolysaccharides in the granulation tissue of wounds, which is of great importance in the formation of the collagen fibrils. This stimulating action is clearly superior to the one obtained with other topical compositions containing lysozyme, like creams or ointments, for example.

The lysozyme gels, as embodied in the present invention, are particularly useful as a body sanitizer and disinfectant, like, for example, in the disinfection of the skin, during pre- and post-surgery, in plastic and aesthetic surgery; in aesthetic surgery for facial care and the care of hands, feet, nails; in the hygiene of hands and of the oral cavity.

The lysozyme gels embodied in the present invention are also useful for sanitizing and disinfecting tools and equipment, objects, environments, like, for example, in hospitals, emergency rooms, shops, food stores, and homes.

The lysozyme gels embodied in the present invention are useful in cosmetics; like, for example before and after depilation, before and after shaving, in facial cleansing and so on. As mentioned above, the lysozyme gels embodied in the present invention have shown to have a favorable influence on the biochemical-metabolic mechanisms at the base of the healing process thanks to its activity promoting the synthesis of mucopolysaccharides and, consequently, the collagen fibrillogenesis.

To the lysozyme gels embodied in the present invention one can add complementary active compounds, either synthetic or natural, as long as they are compatible, like, for example: cicatrizing compounds, disinfectants, antibiotics, antifungals, antivirals, anti-inflammatory agents, vitamins, enzymes, botanical extracts, etc. In particular, essential oils can be used without the employment of solubilizing substances (which are potentially harmful), thus exploiting an additional use of the solvents (such as alcohols) employed in the gel.

Similarly, also natural and synthetic excipients can be added, as long as they are compatible; for example: water (sea-water, thermal water, etc.), alcohols, lipids, glycols, gelling and suspending agents, emulsifiers, thickeners, inert powders, polymers, sweeteners, flavors, flagrances, perfumes, dyes, preservatives, sequestering agents, compounds favoring the absorption of epithelial and connective tissue. Denaturants of ethanol can also be added.

EXAMPLES

In order to illustrate the present invention; we describe some examples of implementation below:

Example 1

Four (4) grams of lysozyme hydrochloride were added to 80 grams of absolute ethanol under stirring; then 20 grams of distilled water were added to the suspension: after brief stirring the suspension of crystalline solid changed into a transparent, colorless, dense gel.

Example 2

Four (4) grams of lysozyme hydrochloride were added to 70 grams of absolute ethanol under stirring; then 30 grams of distilled water were added to the suspension: after brief stirring the suspension of crystalline solid changed into a transparent, colorless, semi-dense gel.

Example 3

Four (4) grams of lysozyme hydrochloride were added to 60 grams of absolute ethanol under stirring; then 40 grams of distilled water were added to the suspension: after brief stirring the suspension of crystalline solid changed into a transparent, colorless, fluid gel.

Example 4

Four (4) grams of lysozyme hydrochloride were added to 80 grams of 91% isopropyl alcohol under stirring; then 20 grams of distilled water were added to the suspension: after stirring and heating to above 60 degrees Celsius, the lysozyme fully dissolved and the suspension of crystalline solid changed into a transparent, colorless, semi-dense gel after cooling down.

Example 5

The pre- and post-operative therapy of 20 phlebopathic patients with active trophic lesions integrated local applications of the lysozyme gel composition of Example 3 for a period ranging from 15 to 30 days. The twenty (20) subjects were suffering from trophic lesions and ulcerative lesions of the lower limbs for varicose veins or post-phlebitis associated with diffuse edema, paresthesias, pain, perifocal eczema etc. These lesions were established for several months (and in some cases for years) and had been treated with different therapies with no benefit. In several patients with bilateral varicose sores it was possible to create a highly demonstrative comparison. After the limbs were placed in a suitable location for the venous drainage, the sores of one extremity were treated locally with the lysozyme gel, while the sores of the opposite limb were treated with one of the conventional products (application of antiseptics, antibiotics, etc.).

Upon treatment, a rapid and spontaneous cleansing of the lesions from debris and from serumpurulent secretion was observed. Subsequently, a gradual but complete disappearance of local inflammatory signs (intumescence, redness, infiltration of the margins, perifocal hyperthermia, etc.) was observed. The typically observed extensive loss of deep tissue (as opposed to surface tissue), did progressively decrease and was rapidly followed by the surprisingly rich formation of granulation tissue, capable of filling in these ulcerations within a short time, thus reaching the complete "restitutio ad integrum" of the injured part. Such improvements were even observed in ulcerations dating back for a long time. In the ulcers from the opposite limb, treated with standard methods, the cleaning first, and then the revival and the granulation of the tissues occurred slowly and rather poorly.

At one-month and one-year check-ups, treated subjects did not complain of any discomfort attributable to circulatory failure. The pain was completely gone, even after long periods of standing and after walking. The data obtained show that the lysozyme gel applied locally determines a favorable healing action of ulcers and lesions of dystrophic nature in general. Although in this therapeutic process, the known lysozyme properties, such as the ability of bacterial lysis and pharmacological properties, namely the anti-inflammatory, anti-edema, and anti-adherence properties may play a role, we believe that the healing action of the lysozyme gel is surprisingly carried out indirectly, in the sense that it prepares and anticipates the healing process and favors it, by continuously cleansing the ulcers from the constant debris and from the eventual bacterial infections. Overall, the lysozyme in gel form proved to be highly active demonstrating surprising healing features.

Example 6

The experiment was conducted using the composition of the lysozyme gel of Example 3. Twenty-four (24) rabbits, each weighing about 2 kg, were kept under the same conditions of nutrition and overall care. A longitudinal linear incision of approximately 8 cm was performed on the medial abdominal region (affecting the skin and subcutaneous tissue up to, but excluding, the facial plane) of each animal under anesthesia and under aseptic conditions. The wound was then sutured with silk sutures equidistant from each other at 1 cm. The animals were divided into 2 groups of 12 rabbits each. Those of the first group were treated with the lysozyme gel; those of the second group were treated with lysozyme ointment (20 mg) and kept as a control.

On the fourth and eighth day weight tension was applied on the scars from these applied wounds by removing a square of the abdominal wall with affecting the skin and subcutaneous tissues, including the wound from which the stitches were first removed. This square of tissue was divided into rectangular strips of 1 cm wide, perpendicular to the wound. At one end of these strips a small scale while was applied while the other end was fixed to a wooden pole. The weight on the scale was gradually increased until the scar detached. The weight at which the scar under examination detached was considered as the "index of resistance", i.e. "index of healing." With a few of the strips, following formalin fixation and the inclusion of paraffin, histological and histochemical samples were prepared.

Tensile Tests— on the fourth day, the indices of wound healing, for both the first and second group of animals, are nearly the same. The average index differs less than 5% with a rupture tension of 110 grams for the control and 105 grams for animals treated with lysozyme gel. On the eighth day, however, the average index clearly shifts in favor (with an almost 23% improvement) of the animals treated with lysozyme gel: a rupture tension of 446 grams versus of 364 grams for the controls.

The results from these tensile tests are reported in the following table:

| Group I - Test Treatment | | | | Group II - Control | | | |
| --- | --- | --- | --- | --- | --- | --- | --- |
| Subject # | Treatment | Day of Study | Index of Healing (grams) | Subject # | Treatment | Day of Study | Index of Healing (grams) |
| I-1 | Lysozyme Gel | 4 | 80 | II-1 | Ointment | 4 | 120 |
| I-2 | Lysozyme Gel | 4 | 110 | II-2 | Ointment | 4 | 80 |
| I-3 | Lysozyme Gel | 4 | 110 | II-3 | Ointment | 4 | 120 |

| Group I - Test Treatment | | | | Group II - Control | | | |
|---|---|---|---|---|---|---|---|
| Subject # | Treatment | Day of Study | Index of Healing (grams) | Subject # | Treatment | Day of Study | Index of Healing (grams) |
| I-4 | Lysozyme Gel | 4 | 105 | II-4 | Ointment | 4 | 90 |
| I-5 | Lysozyme Gel | 4 | 115 | II-5 | Ointment | 4 | 140 |
| I-6 | Lysozyme Gel | 4 | 120 | II-6 | Ointment | 4 | 11 |
| Average Day 4 | | | 106.7 | Average Day 4 | | | 93.5 |
| I-7 | Lysozyme Gel | 8 | 350 | II-7 | Ointment | 8 | 370 |
| I-8 | Lysozyme Gel | 8 | 530 | II-8 | Ointment | 8 | 300 |
| I-9 | Lysozyme Gel | 8 | 480 | II-9 | Ointment | 8 | 320 |
| I-10 | Lysozyme Gel | 8 | 400 | II-10 | Ointment | 8 | 340 |
| I-11 | Lysozyme Gel | 8 | 470 | II-11 | Ointment | 8 | 500 |
| I-12 | Lysozyme Gel | 8 | 450 | II-12 | Ointment | 8 | 360 |
| Average Day 8 | | | 446.7 | Average Day 8 | | | 365.0 |

Macroscopic Findings—

While all the wounds of the first group did heal perfectly with no suppurative activities, in 9 of 12 rabbits in the control group, the wounds showed clear inflammatory processes with a few areas of suppurative inflammation and necrosis. In these cases we selected, both for the tensile tests and for the microscopic examinations, strips of wall concerning scars free of suppuration.

Histological Findings—

On the fourth day there was plenty of fresh granulation tissue in all animals alike, but this was moderately infiltrated by inflammatory elements in the group treated with the lysozyme gel, while the inflammatory phenomena are most evident in the controls, with infiltration of numerous granulocytes, and mononuclear and histiocytes elements. On the eighth day, in animals treated with the lysozyme gel, we found acanthosis and hypercanthosis of the epidermis with and evident increase of the granulation; in samples the collagen fibers of the dermis which branched out like a fan in bands parallel with elements of uniform thickness; newly formed capillaries were numerous, with limited inflammation; the elastic fibers in the granulation tissue were slightly pale. In a comparative examination of the control animals the following was found: a more modest acanthosis and hypercanthosis with less evident increase of the granular state; more irregular in orientation and thickness the collagen bands which are more spaced between them; present, and in certain points, numerous poly- and mono-nucleated elements, no significant difference in the amount and behavior of newly formed capillaries and elastic fibers.

Histochemical Findings—

The metachromatic interstitial substance, highlighted with toluidine blue, in animals treated with lysozyme gel was very abundant on the fourth day, while it decreased significantly on the eighth day. Conversely in the control animals this substance is modestly present on the fourth day, while is more abundant on the eighth day.

By examining the obtained data the following observations were made: Surprisingly, the lysozyme gel exerts a more positive influence on the development of wounds, which were all perfectly healed by first treatment in contrast to what occurred with the control. The macroscopic data correspond to the histological data demonstrating limited inflammation in the gel treated samples, and in any case less than in the control. In animals treated with the lysozyme gel the metachromatic substance, which indicates the presence of mucopolysaccharides, and which was abundant on the fourth day, was poorly represented on the eighth day; exactly the opposite from the control animals. Lysozyme gel thus enhances the synthesis of mucopolysaccharides, which are of great importance in the formation of collagen fibrils. The collagen fibrils were more numerous on the eighth day in the gel treated rabbits than in the control rabbits, confirming the close relationship between the rate of synthesis of mucopolysaccharides and the extent of collagen fibrillogenesis that follows the treatment. The histological and histochemical results also explain the results of tensile tests, i.e.: there were only limited differences between the two groups of animals on the fourth day, when the collagen fibrils had not yet appeared; on the eighth day, instead, the scars treated with the lysozyme gel, in which collagen fibrils were more numerous, had higher resistance values than the scars of the control animals.

Example 7

A patient diagnosed with Grade 3 acne was treated with the lysozyme gel of Example 3 on one half of his back with and with topical erythromycin on the other half of his back for five days. After 5 days of therapy, the acne treated with topical erythromycin showed moderate improvement while the acne treated with the lysozyme gel disappeared completely.

What is claimed is:

1. A composition comprising a gel formed at least in part as a result of a gel-forming interaction between solid lysozyme, water and a liquid organic solvent, wherein the gelled lysozyme retains at least one enzymatic activity, wherein the organic solvent is miscible with water but one in which lysozyme does not substantially dissolve, and wherein the composition does not include gelling substances besides the lysozyme.

2. The composition according to claim 1, wherein the organic solvent is an alcohol.

3. The composition according to claim 2, in which the alcohol is selected from the group consisting of ethanol, methanol, propanol, butanol, isopropyl alcohol, isobutyl alcohol, isoamyl alcohol, benzylalcohol, and polyvinylalcohol.

4. The composition according to claim 1, in which the organic solvent is selected from the group consisting of dioxane, mercaptoethanol and acetonitrile.

5. The composition according to claim 1, in which the lysozyme is a free base.

6. The composition according to claim 1, in which the lysozyme is a salt.

7. The composition according to claim 6, in which the lysozyme is an organic salt.

8. The composition according to claim 6, in which the lysozyme is an inorganic salt.

9. The composition according to claim 8, wherein the inorganic salt is hydrochloride.

10. The composition according to claim 1, in which the lysozyme is hen-egg-white lysozyme.

11. The composition according to claim 1, in which the lysozyme is recombinant human lysozyme.

12. The composition according to claim 1, which additionally comprises one or more additional active ingredients selected from the group consisting of cicatrizing compounds, disinfectants, antibiotics, antifungals, antivirals, anti-inflammatory agents, vitamins, enzymes, botanical extracts and essential oils.

* * * * *